United States Patent [19]
Delk et al.

[11] Patent Number: 5,356,426
[45] Date of Patent: Oct. 18, 1994

[54] REFILLABLE ICE PACK

[75] Inventors: Robert E. Delk, Dallas; Michael L. Bowen, Arlington, both of Tex.

[73] Assignee: Struckmeyer Corporation, Dallas, Tex.

[21] Appl. No.: 45,360

[22] Filed: Apr. 13, 1993

[51] Int. Cl.$^5$ .............................................. A61F 7/04
[52] U.S. Cl. .................................... 607/112; 607/114
[58] Field of Search ............... 128/96, 104, 108–112, 128/114

[56] References Cited

U.S. PATENT DOCUMENTS

| | | | |
|---|---|---|---|
| 1,313,021 | 8/1919 | Scott | 607/112 |
| 1,752,808 | 4/1930 | Reach . | |
| 2,043,327 | 6/1936 | Miller . | |
| 2,273,128 | 2/1942 | Madsen et al. | 607/114 X |
| 3,244,210 | 4/1966 | Clarizo . | |
| 3,299,927 | 1/1967 | Clarizo . | |
| 3,356,086 | 12/1967 | Behney . | |
| 3,368,984 | 3/1975 | Jorgensen . | |
| 3,867,939 | 2/1975 | Moore et al. | 607/104 X |
| 3,874,504 | 4/1975 | Verakas . | |
| 3,893,834 | 7/1975 | Armstrong . | |
| 4,033,354 | 7/1977 | DeRosa . | |
| 4,149,541 | 4/1979 | Gammons et al. . | |
| 4,159,728 | 7/1979 | Kraus et al. | 607/114 X |
| 4,347,848 | 9/1982 | Hubbard et al. . | |
| 4,385,950 | 5/1983 | Hubbard et al. . | |
| 4,408,643 | 10/1983 | Laske et al. . | |
| 4,867,230 | 9/1989 | Voss | 607/104 X |
| 4,951,666 | 8/1990 | Inman et al. . | |
| 5,074,300 | 2/1991 | Murphy . | |

Primary Examiner—Angela D. Sykes
Attorney, Agent, or Firm—Richard C. Litman

[57] ABSTRACT

An ice pack having a reservoir, a large mouth, and a narrow neck intermediate the mouth and the reservoir. The mouth is tapered to a form funnel to permit the reservoir to be easily filled. A variance in heat exchange is provided between the opposing sides of the ice pack. Hence, one side is significantly colder than the other. Each side includes an identifiable visual characteristic which distinguishes one side from its opposite side, thus enabling an observer to determine which side of the two sides is in communication with a localized region of a patient requiring treatment. A formable element implanted within the structure of the ice pack proximate mouth enables the mouth to be easily formed into the shape of the aforementioned funnel. A safety clip is clamped upon the neck of the ice pack to retain its contents in the reservoir separate from the mouth. The clip includes a safety lock that prevents the two components from inadvertently disengaging if its hinge becomes damaged and broken. A plurality of ties extend laterally of a longitudinal axis of the ice pack and facilitate maintaining the ice pack against the localized region receiving treatment. A method is prescribed in which the opposing sides of the ice pack is heat sealed and simultaneously die cut along the seal, thus eliminating the two step process, namely, sealing and then cutting or tearing.

28 Claims, 8 Drawing Sheets

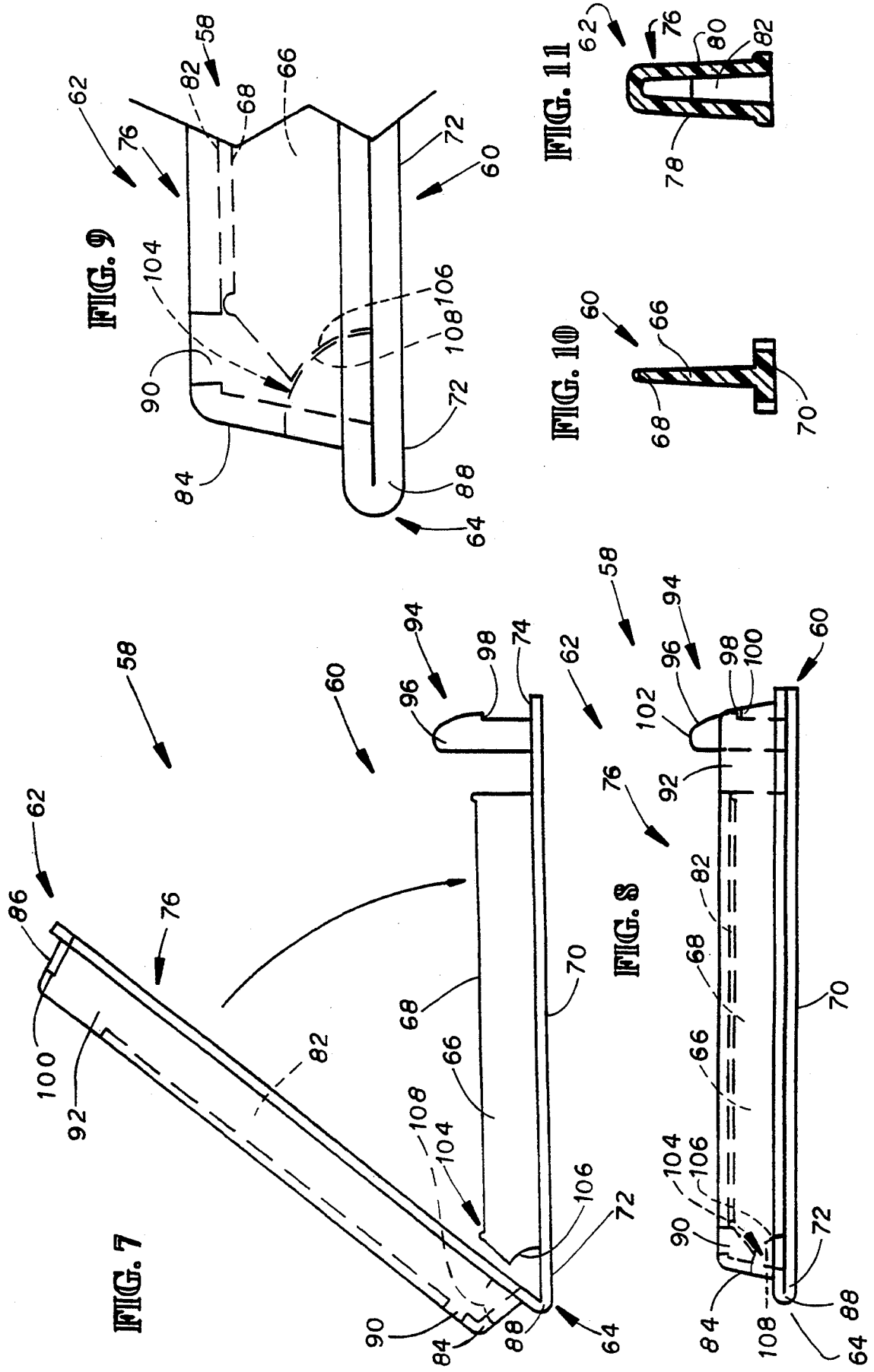

REFILLABLE ICE PACK

BACKGROUND OF THE INVENTION

1. Field of the Invention

The present invention relates generally to surgery and more particularly, to body member enclosing thermal applicators.

2. Description of the Prior Art

It is a standard therapeutic procedure to treat specific injuries, such as sprained or strained muscle tissues, by chilling a localized region to reduce swelling and discomfort. Ice packs of diverse forms are available for administering to localized injuries. These are modest, specialized ice packs, typically housing a pouch for retaining ice and a strap or a pair of straps for maintaining the pouch in contact with the localized area to be attended. These ice packs are rather fragile and, as a result of their size, have a pouch opening of limited dimensions which makes it difficult to fill the pouch from an ice machine or with an ice scoop. Consequently, ice is frequently spilled as the pouch is filled and/or damage to the delicate ice pack occurs.

There is a demand for an ice pack having an opening of considerable size so as to permit the pack to be effortlessly filled. Preferably, the opening would be fashioned into the shape of a funnel. In other words, the funnel would unfold upon grasping the ice pack in a specific manner. U.S. Pat. Nos. 4,347,848, issued Sep. 7, 1982, and 4,385,950, issued May 31, 1983, both to Vance M. Hubbard et al., disclose an outwardly diverging throat proximate the opening of an ice pack and a disposable funnel to be inserted therein. Nonetheless, Hubbard et al. does not disclose an opening which may be modeled into the shape of a funnel. U.S. Pat. No. 4,951,666, issued Aug. 28, 1990 to Joel D. Inman et al., describes a flap for creating a chute to facilitate filling an inner bag with ice. This is accomplished by pursing the bag side edges and open top. The employment of an element bordering the opening which, by manipulation, could serve in styling the opening into the shape of a funnel would provide a significant advancement beyond the teachings of the Inman et al. patent. U.S. Pat. Nos. 3,368,984, issued Mar. 4, 1975 to Blanche I. Jorgensen, and 4,408,643, issued Oct. 11, 1983 to Louis L. Laske et al., each disclose a stiffener strip associated with the mouth. However, these strips function as closure devices and are not used to form funnels. An opening which may be easily formed into the shape of a funnel has not as of yet been devised.

There is also a demand for an ice pack which provides a variance in heat exchange in accordance with its application. For example, some patients are intolerant to cold temperatures and the use of a conventional ice pack will inflict an inordinate amount of discomfort upon the patient. In certain circumstances, the utilization of a traditional ice pack will be too cold, possibly placing the patient's health in jeopardy. In other instances, a very cold ice pack may be necessitated. Then, there are those situations when a patient is merely desirous of using either a very cold compress or a mildly cool compress. A dual temperature ice pack would allow the needs of all of these conditions to be fulfilled. An ice pack having two sides, one side being more insulated than the other side, would deviate in temperature from side to side. The more insulated side, that is, the warmer side of the two sides, would be applied against the patient when a mildly cool compress is favorable, such as on the forehead of a feverish patient. The lesser insulated side or the colder of the two sides would be used when a cold compress is desired, such as on a sprain. A need exists for a dual temperature ice pack which enables a health care professional or a patient to select a temperature which is most appropriate for a particular application. U.S. Pat. No. 4,408,643, issued Oct. 11, 1983 to Louis L. Laske et al., discloses a plastic bag having one side completely insulated with a poly foam material. U.S. Pat. No. 2,043,327, issued Jun. 9, 1936 to Thomas W. Miller, teaches of a hot water bottle having two sides, each being fabricated different densities of rubber to provide one side having a greater heat exchange rate than the other. It is suggested that the less insulated side is initially too hot to place in contact with the patient's skin. Thus, the more insulated side is initially placed in contact with the patient's skin and, as the content of the bottle decreases in temperature, the less insulated side is placed in contact with the patient's skin, prolonging the use of the hot water bottle. An alternative to the hot water bottle disclosed by Miller above is U.S. Pat. No. 3,874,504, issued Apr. 1, 1975 to John P. Verakas, describing a gel filled cold pack having a poly foam insulating layer on only one side. The cold pack is configured to insulate only the side which is exposed to the ambient environment, thus allowing the contents of the cold pack to remain cold longer. Hence, the cold pack, as described by Verakas, has a cold side and a completely insulated side. An ice pack having a cold side and a mildly cool side has yet to be introduced.

Equally important, if such an ice pack had one side which possessed a characteristic visually distinct with respect to the other side, such as a color disparity, an exemplary pattern or symbol, or one or more characters denoting an identifying word or phrase, such as "cool" and "cold", the health care professional would be able to distinguish visually the two sides from one another, even at a distance.

Yet another matter to be considered in the development of ice packs is an efficient manner of manufacture. Various types of construction and methods thereof are employed in manufacturing ice packs. For example, U.S. Pat. Nos. 3,244,210, issued Apr. 5, 1966, and 3,299,927, issued Jan. 24, 1967, both to Giacomo Clarizo, show the sealing of a bag within a rectangular envelope through the use of plural seals, one of which is a heat seal for producing a cut and tear construction. U.S. Pat. No. 4,385,950, issued May 31, 1983 to Vance M. Hubbard et al., describes an ice pack having an absorbent intermediate layer. The ice pack is formed by ultrasonic welding methods. A funnel is sonically welded thereto. Hubbard et al. discloses a method of forming an ice pack comprising the steps of: positioning strips of three ply material; two subsequent ultrasonic steps to form an envelope; and two subsequent cutting steps to form strips parallel to the sides of the envelope. U.S. Pat. No. 3,893,834, issued Jul. 8, 1975 to Arthur E. Armstrong, discloses an insulated cold pack comprising four sheets of polyurethane heat sealed to one another along their edges. U.S. Pat. No. 4,149,541, issued Apr. 17, 1979 to Clifford E. Gammons et al., shows a hot or cold fluid circulating pad formed of four panels sealed together by a thermoplastic process. Two inner panels forming a bag are of a thermoplastic material and two outer panels forming a outer covering are of a fabric material. The bag is clearly formed internally of the outer fabric covering. U.S. Pat. No. 4,951,666, issued Aug. 28, 1990 to Joel D. Inman et al., discloses a thermal pack having a cloth outer bag, a separate plastic inner bag, a plastic filling flap, a cuff, a zip lock closure, and a velcro closure. U.S. Pat. No. 5,074,300, issued Dec. 12, 1991 to Edward Murphy, discloses a tearing of a complete bag along from a length of stock material used to form bags, as a replacement for a separate die cutting operation to separate the completed bags. A tear line is formed by a sharpened heating element. Also discussed is a no-tear seam, a tapered edge, and a fibrous heat seal.

While in the main, prior art ice packs are manufactured implementing myriad materials and techniques, there remains a need for a less expensive and more efficiently produced ice pack and a method of manufacturing the same which reduces the number of costly manual steps involved. Ideally, an ice pack construction in which the ice pack is formed by thermoplastically welding its edges while simultaneously cutting the same proximate the weld, and thus eliminating the requirement of a cutting step in succession with sealing step would meet such a requirement. It would be advantageous for such an ice pack to include a funnel forming element along the mouth of the opening thereof. It would be further beneficial to attach lateral strips to the top and the bottom of the ice pack for maintaining the same adjacent the patient's skin.

Aside from the above mentioned patents, another patent which is of interest is U.S. Pat. No. 4,347,848, issued Sep. 7, 1982 to Vance M. Hubbard et al., disclosing tie strings which are longitudinally disposed and inwardly offset. The straps to be disclosed hereinafter in accordance with applicants' instant invention extend laterally from the longitudinal axis of the ice pack. U.S. Pat. No. 1,752,808, issued Apr. 1, 1930 to Milton B. Reach, disclosing a bag having a strap type devices also considered to be of interest. The strap, however, is located proximate the mouth of the bag and is a part of a closure mechanism, rather than being an element for maintaining the position of the bag as is the intended use of the strap disclosed by applicants. Other patents which are of interest include U.S. Pat. Nos. 3,356,086 issued Dec. 5, 1967 to Charles A. Behney and 4,033,354 issued Jul. 5, 1977 to Maria De Rosa.

It should be noted that none of the above patents, taken either singly or in combination, is seen to describe the instant invention as claimed.

SUMMARY OF THE INVENTION

The present invention is related to an ice pack having a reservoir for storing ice or ice water therein, having a large mouth for receiving the ice or ice water therethrough, and having a narrow neck intermediate the mouth and the reservoir to permit the passage of ice or ice water therethrough from the mouth to the reservoir. Preferably, the width of the neck opening is squared off so as to be restricted and the mouth is tapered to provide an entry funnel for the ice or ice water to pass easily therethrough.

Preferably, the ice pack is fabricated of opposing sides of multi-layered, pliable material sealed along the bottom and side edges of the reservoir, along the side edges of the neck, and along the bottom and side edges of the mouth so as to form an opening along the top of the mouth. The opposing sides of the ice pack each include an inner layer of sheet material impervious to liquids, an outer layer of non-woven absorbent material, and an intermediate layer of perforated, non-absorbent sheet material wherein the intermediate layer of one side of the ice pack has either larger perforations or a greater number of perforations than the intermediate layer of the opposing side of the ice pack so as to provide a variance in heat exchange between the opposing sides and, in turn, a variance in temperature. The intermediate layers of each side deliberately lack wicking and absorption properties. Each side may include an identifiable visual characteristic which distinguishes one side from the opposite side. For example, a first side may be a first color, such as white, and a second side, opposite the first side, may be a second color, such as blue. The first and second colors, respectively, would be indicative of the first and second temperatures corresponding to the temperature variation between the opposing sides.

Formable elements, such as plastic stays or encapsulated wires, implanted within the structure of the ice pack proximate mouth, enable the mouth to be easily formed into the shape of the aforementioned funnel. The formable elements may be embedded between certain of the layers of the multi-layered material bordering the opening of the mouth. By manipulating the formable element, the opening is selectively opened and closed so as to create and retract the funnel. In other words, the funnel would open upon grasping the neck and mouth and would close flat upon release of the neck and the mouth. In the closed or flattened posture, the funnel is foldable so as to be concealed or retained, such as in a pocket or beneath a strap adjacent the reservoir.

A jackknife type safety clip is clamped upon the neck of the ice pack to retain the ice or ice water in the reservoir separate from the mouth. The clip is comprised of first and second components connected together by a living hinge which includes a safety lock that prevents the two components from inadvertently disengaging if the hinge becomes damaged and broken.

A plurality of ties in the form of strips or straps extend laterally of a longitudinal axis of the ice pack. The ties facilitate maintaining the ice pack against the localized region receiving treatment.

The ice pack is fabricated by first perforating a length of two separate sheets of foam material, such as with a rotary perforating machine, each length of foam material being perforated distinctly from one another. The lengths of foam material are each wound on rollers. Subsequently, a plurality of rolls of material are layered together, two rolls of which are the previously perforated lengths of foam material. The rolls are layered on a heat sealing and cutting machine with at least two inner polyethylene watertight layers juxtaposed one another, a perforated poly foam layer adjacent each inner layer, and at least one non-woven material outer layer contiguous to each poly foam layer. The poly foam layers do not extend beyond the juncture of the reservoir and the neck. Prior to sealing and cutting the edges, the top edges of each inner and outer layer bordering the opening of the mouth are folded in opposing directions over respective forming elements which are then sealed, such as with a rotary sealer, a heat sealer, or a sonic sealer, inside these opposing folds. At this juncture, we have a mouth and neck formed of two plies of at least two layers, each ply having forming elements enclosed in a fold adjacent the edges which cooperatively form the opening, and a reservoir formed of two plies of at least three layers. These two plies are then heat sealed together along the bottom and side edges so as to form the shape of a dumbbell and are simultaneously die cut along the seal to produce the ice pack according to the present invention.

Accordingly, it is a principal object of the invention to provide an ice pack having a reservoir, a large mouth, and a narrow neck intermediate the mouth and the reservoir to permit the passage of ice or ice water therethrough from the mouth to the reservoir.

Another object is to provide a squared off, restricted neck opening and a tapered mouth to produce an entry funnel for the ice or ice water to pass therethrough and thus, provide an ice bag which is easy to fill.

A further object is that the ice pack be fabricated of opposing sides which provide a variance in heat exchange and, in turn, a variance in temperature therebetween.

Yet another object is to employ an identifiable visual characteristic which distinguishes one side from the other side so as to permit the temperature differential between the opposing sides to be visually determined.

Still another object is to incorporate a formable element which may be manipulated to enable the opening of the mouth to be selectively opened and closed so as to create and retract a funnel.

It is another object that a closure clip be attachable about the neck of the ice pack, to retain the ice or ice water in the reservoir.

It is further an object that a plurality of ties extend laterally of a longitudinal axis of the ice pack to facilitate holding the ice pack against the localized region receiving treatment.

It is an object to provide a method in which opposite sides of an ice pack are each formed of a separate ply including at least one watertight inner layer, at least one outer layer, and a uniquely perforated intermediate foam layer between the inner and outer layers.

It is another object to provide a method in which a formable element is heat sealed within opposing severed folds proximate the leading edge of the two plies.

It is yet another object to simultaneously heat seal and die cut the two plies so as to form the ice pack.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 7 is a side elevational view of the safety clip used in combination with the ice pack in an open condition.

FIG. 8 is a side elevational view of the safety clip shown in FIG. 7 in a closed condition.

FIG. 9 is a partial side elevational view of the safety clip shown in FIG. 8 detailing the safety lock feature of the hinge.

FIG. 10 is a cross-sectional view of the wedge-shaped blade of the safety clip.

FIG. 11 is a cross-sectional view of the sheath of the safety clip shown.

Similar reference characters denote corresponding features consistently throughout the attached drawings.

DETAILED DESCRIPTION OF THE PREFERRED EMBODIMENTS

Figure 1:
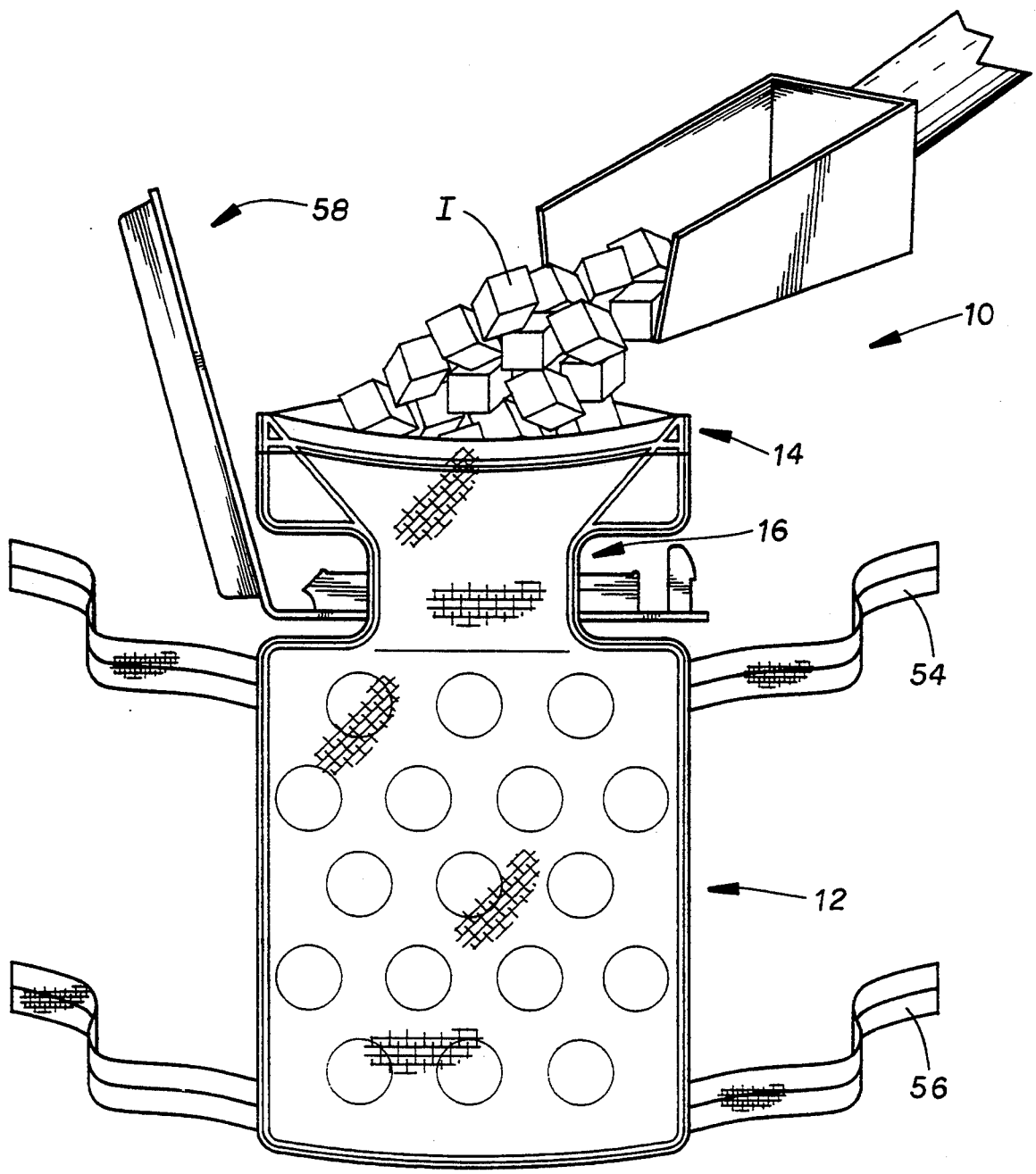
FIG. 1 is an elevational view of one side of an ice pack according to the present invention.
Figure 2:
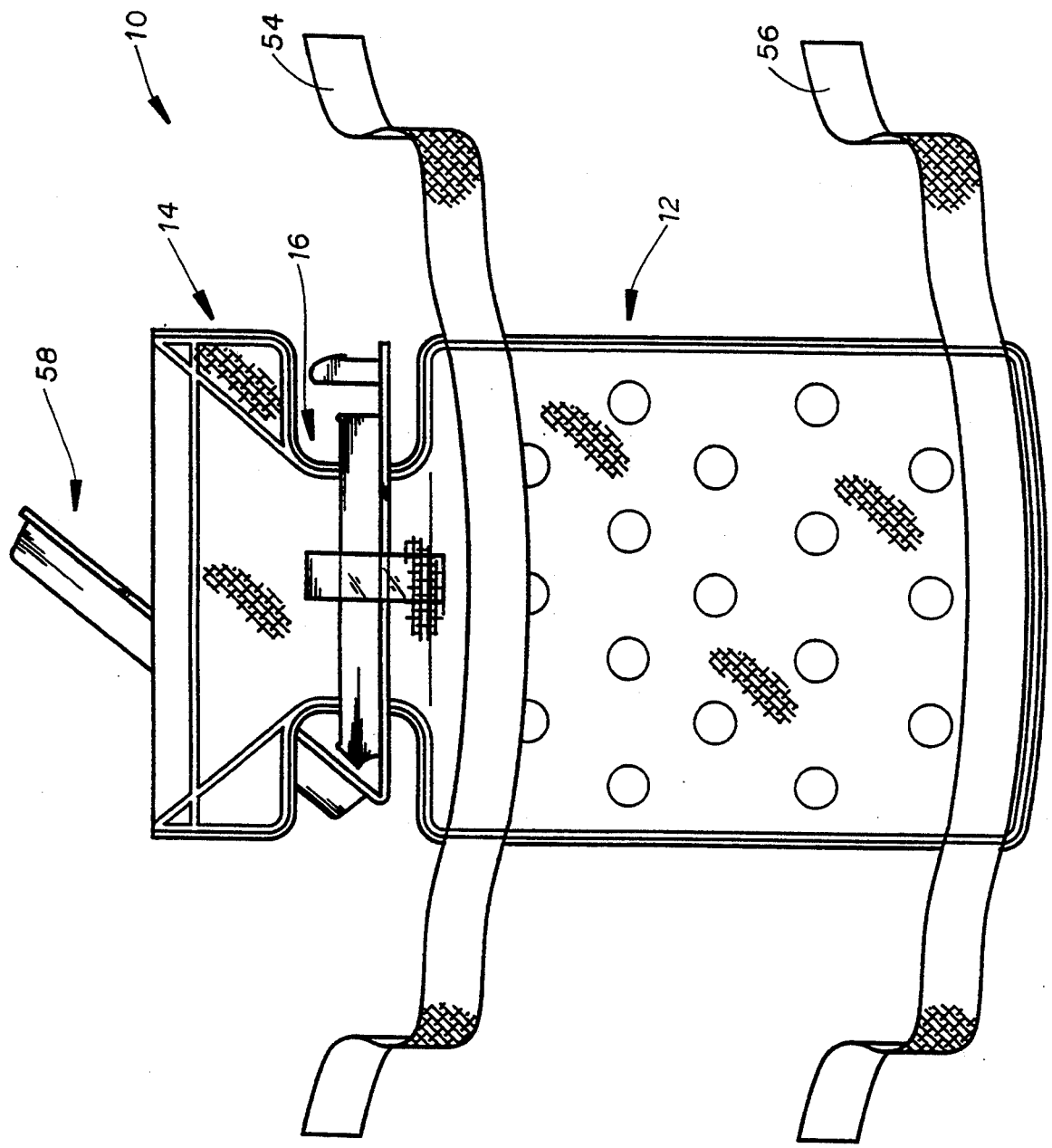
FIG. 2 is an elevational view of an opposite side of the ice pack shown in FIG. 1.
Figure 3:
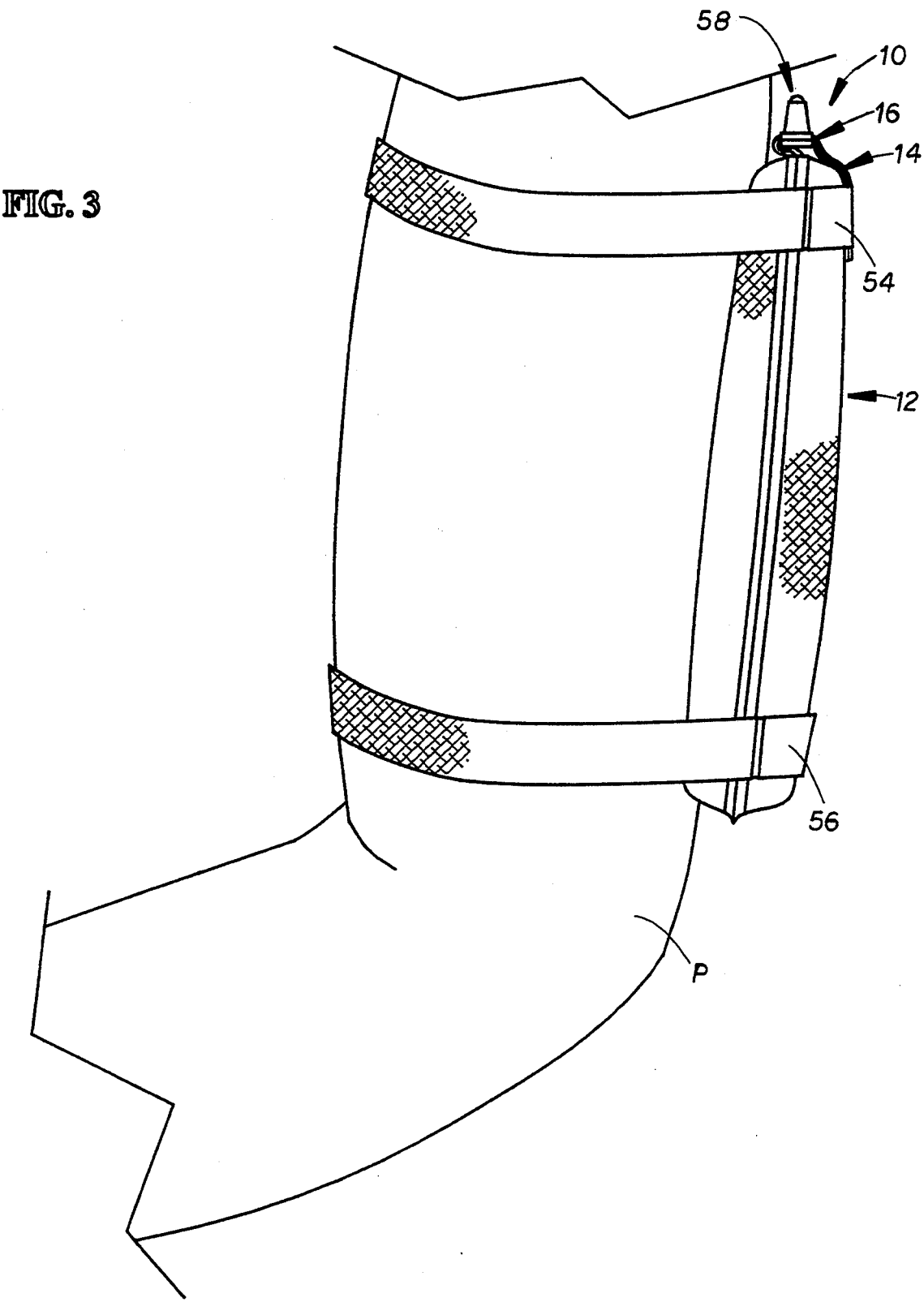
FIG. 3 is an environmental view of the ice pack shown in FIG. 1.

Now referring to the drawings and, in particular, to FIGS. 1 through 3, there is shown of an ice pack 10 in accordance with the present invention. The ice pack 10 has a reservoir 12 for storing ice I or the like therein, a large mouth 14 for receiving the ice I therethrough, and a narrow neck 16 intermediate the mouth 14 and the reservoir 12 to permit the passage of the ice I therethrough from the mouth 14 to the reservoir 12. Preferably, the width of the neck 16 is restricted by its squared off opening 18, and the mouth 14 is tapered to provide an entry funnel 20 for the ice I to pass easily therethrough.

Figure 4:
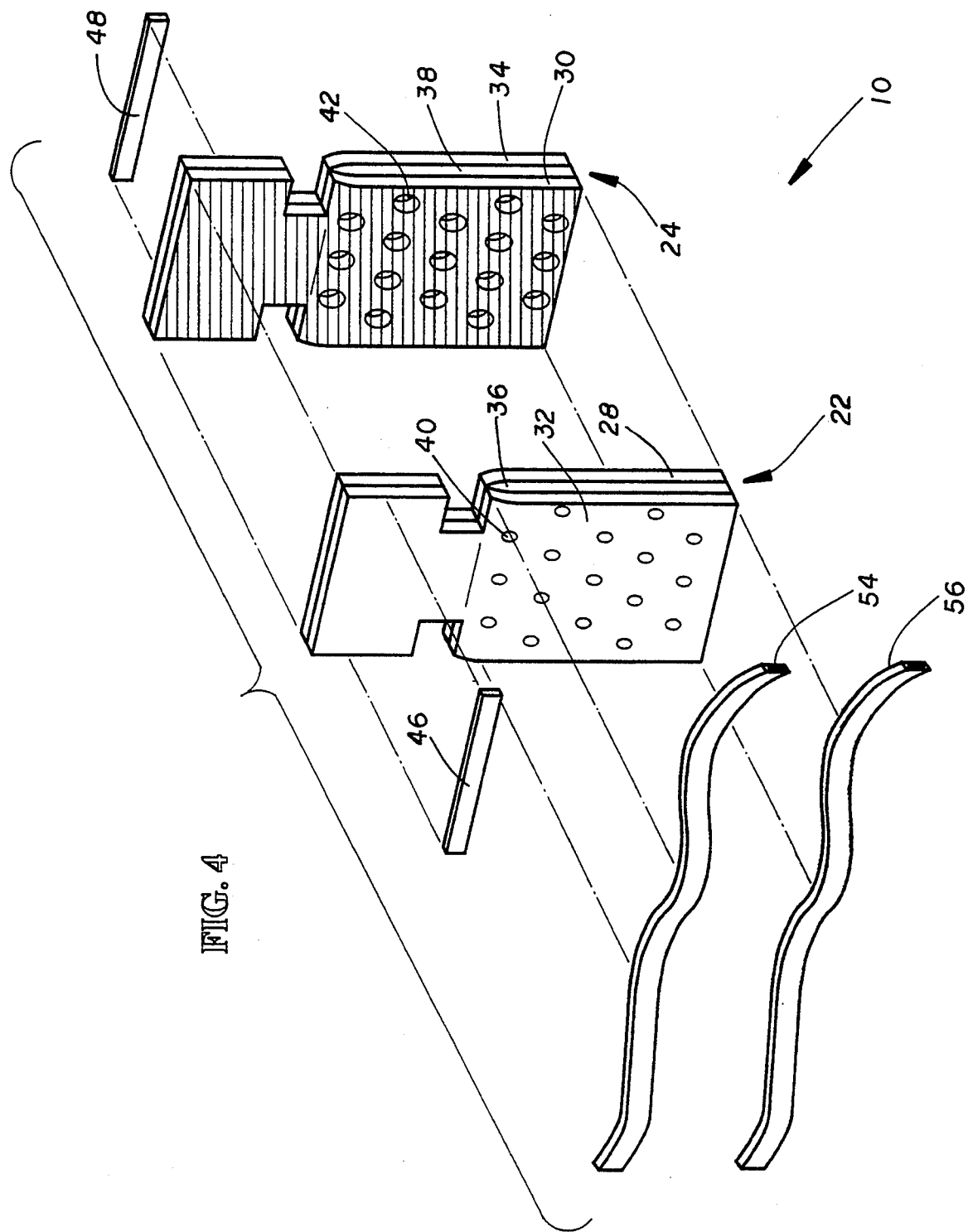
FIG. 4 is a partially exploded perspective view of the ice pack according to the present invention.
Figure 5:
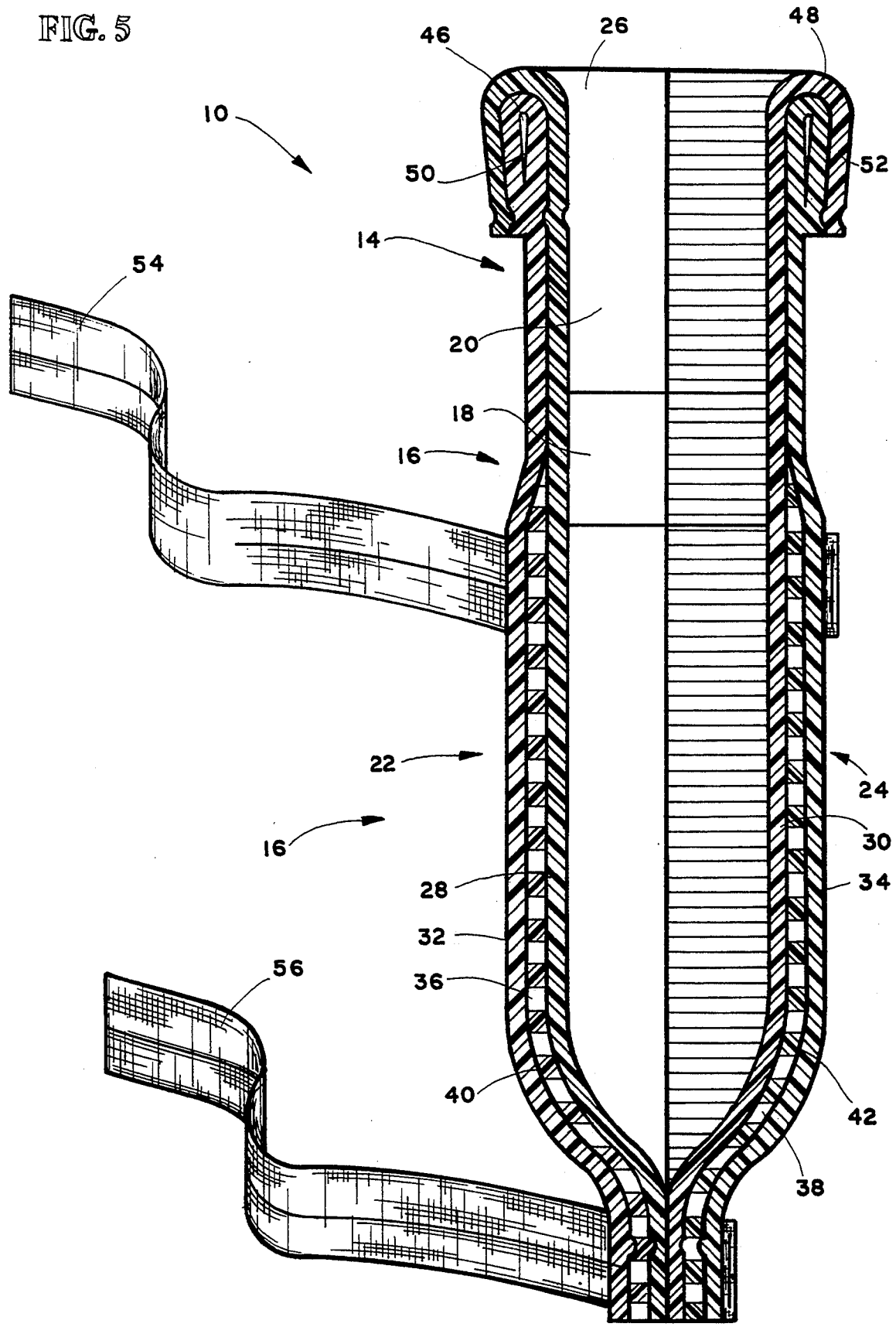
FIG. 5 is a cross-sectional view of the ice pack according to the present invention.

Referring to FIGS. 4 and 5, the ice pack 10 is fabricated of opposing sides 22, 24 of multi-layered, pliable material, sealed along the bottom and side edges of the reservoir 12, along the side edges of the neck 16, and along the bottom and side edges of the mouth 14 so as to yield an opening 26 along the top of the mouth 14 to the funnel 20. The opposing sides 22, 24 of the ice pack 10 each include an inner layer 28, 30, an outer layer 32, 34, and an intermediate layer 36, 38 interposed the inner and outer layers 28, 30 and 32, 34.

Each inner layer 28, 30 is of sheet material impervious to liquids and each outer layer 32, 34 is of a non-woven absorbent material. Preferably, the inner layers 28, 30 are of a poly and outer layers 32, 34 are of a translucent or transparent white, spunlaced polyester, a combination of polyester and rayon, a polyethylene, a spun-bonded polypropylene, or some other suitable non-woven heat sealable material.

The intermediate layers 36, 38 are of a perforated non-absorbent polyethylene foam material. By perforating the foam material with different size holes 40, 42 for each side 22, 24 of the ice pack, one side 22 is more insulated than an opposite side 24; hence the temperature of each side 22, 24 is controlled quite effectively. Alternatively, identically dimensioned holes may vary in number with respect to each side 22, 24. Moreover, the holes 40, 42 could possibly be of some varying shape or shapes, as in the form of indicia.

As shown in FIG. 5, the intermediate layer 38 of one side 24 of the ice pack 10 has larger perforations than the intermediate layer 36 of the opposite side 22, so as to provide a variance in heat exchange rate between the opposing sides 22, 24. This allows a health care professional or patient to treat an injury with the side 22, 24 of the ice pack 10 having a temperature which is most suitable for a particular application, one side 24 being less insulated and substantially colder than the other 22.

As show in FIGS. 4 and 5, each side 22, 24 includes an identifiable visual characteristic which distinguishes one side 22 from its opposite side 24. One side 22 possesses a distinctive characteristic, such as a different color, a recognizable pattern or symbol, or a set of characters denoting an identifying word or phrase. For example, a first side 22 may be a first color, such as white, and a second side 24, opposite the first side 22, may be a second color, such as blue. The first and second colors, respectively, would be indicative of the first and second temperatures corresponding to the temperature variation between the opposing sides 22, 24. To elaborate, the color blue would be representative of the colder side 24 of the two sides 22, 24 and the color white would be indicative of the warmer side 22 of the two sides 22, 24. This could easily be accomplished by employing a blue poly inner layer 30 which may be visually perceived through its respective intermediate and outer layer 38 and 34 and a white or clear inner layer 28 which may be viewed through its respective intermediate and outer layers 36 and 32.

Figure 6:
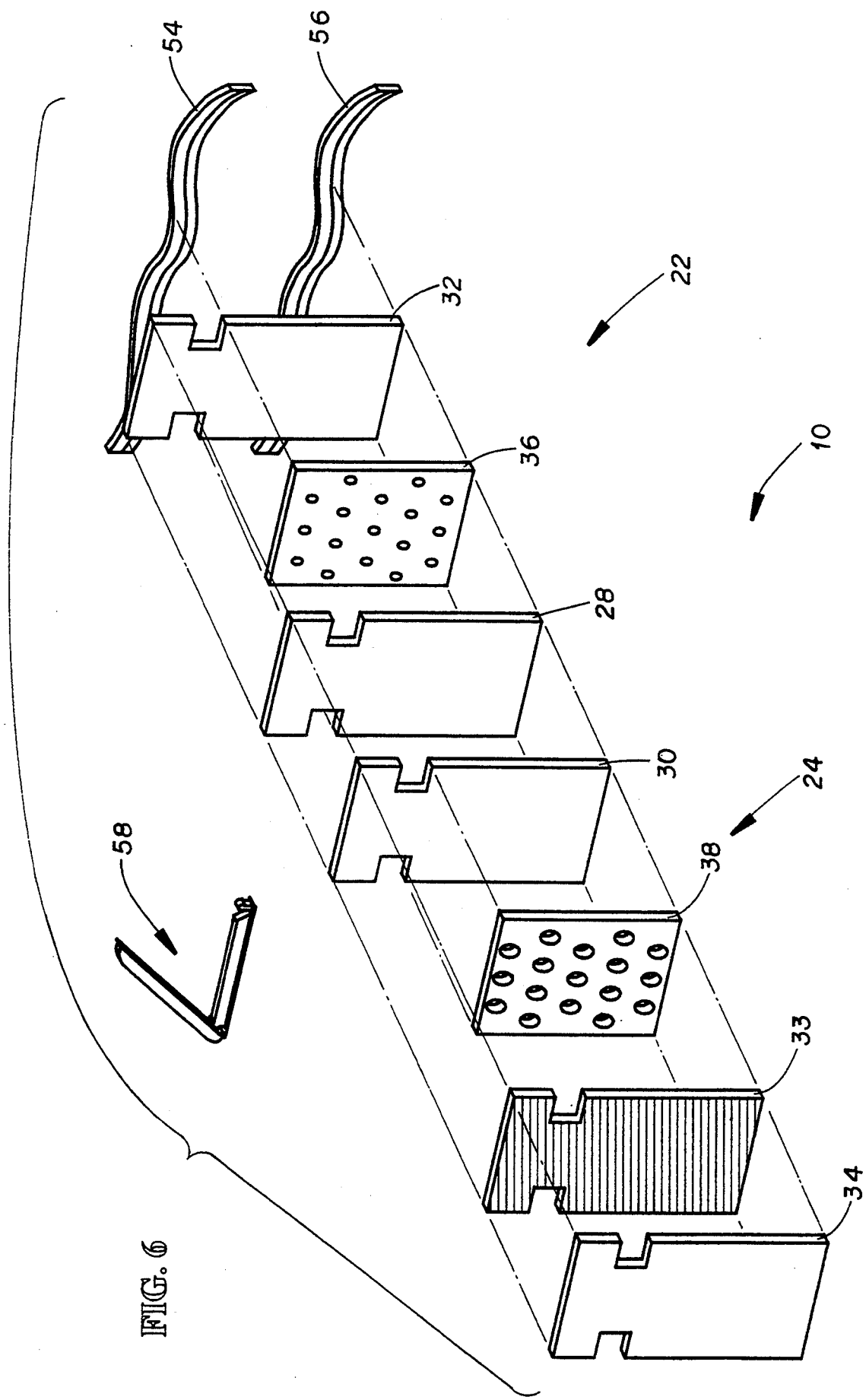
FIG. 6 is a partially exploded perspective view of an alternative ice pack.

An alternative embodiment is shown in FIG. 6. An additional outermost intermediate blue poly layer 33 may be located between its respective intermediate foam layer 38 and outer white polyester layer 34. In this embodiment, the inner and outer layers 28 and 32 of one side 22 would be of the same material as respective inner and outer layers 31, 34 of the opposite side 25.

As another alternative, character sets (not shown) forming words, such as "cold" and "cool", may be employed to identify respective sides 22, 24 or representative symbols (also not shown) may be applied. These characters or symbols would enable a practitioner or a health care professional to discern visually at distance which one of the two sides 22, 24 is placed in contact with the region of the patient P being treated.

Referring back to FIGS. 4 and 5, formable elements 46, 48, such as plastic stays or encapsulated wires, are enclosed within the structure of the ice pack 10 proximate mouth 14 to enable the mouth 14 to be easily formed into the shape of the funnel 20. Preferably, the formable elements 46, 48 are embedded in respective folds 50, 52 formed by the inner and outer layers 28, 30 and 32, 34 of the opposite sides 22, 24. The folds 50, 52 border the opening 26 of the mouth 14 and give upon the manipulation of the formable elements 46, 48. By manipulating the formable elements 46, 48, the opening 26 is selectively opened and closed so as to create and retract the funnel 20. In other words, the funnel 20 is easily opened upon grasping the neck 16 and mouth 14 and is permitted to close flat upon release of the neck 16, and the mouth 14. In the closed or flattened posture, the mouth 14 is foldable so as to be concealed or retained in an unobtrusive attitude, such as in a pocket (not shown) or beneath a strap or tie 54, 56, as shown in FIG. 3, located adjacent the reservoir 12.

As shown in FIG. 3, once the ice pack 10 is filled and the funnel 20 is retracted, and prior to folding the mouth 14 adjacent the reservoir 12, a jackknife type safety clip 58 is clamped upon the neck 16 of the ice pack 10 to retain the ice I in the reservoir 12 separate from the mouth 14.

Referring to FIGS. 7 through 9, the clip 58 is comprised of first and second components 60, 62 hingedly joined together by a living hinge safety lock element 64. One of the components 60 includes a thin, elongated, generally wedge-shaped blade 66 having parallel, longitudinal edges 68, 70 and opposite ends 72, 74. The other component 62 includes a narrow, channel-defining trough or sheath 76 having a generally U-shaped cross-section including opposite ends 84, 86 and side walls 78, 80, as shown in FIG. 11, that are spaced apart to form a channel 82 therebetween. The sheath 76 is configured to receive the blade 66 in a matingly engageable fashion. The cross-section of the blade 66, as shown in FIG. 10, is slightly narrower than that of the sheath 76 so as to enable the blade 66 to fit tightly within the sheath 76.

One of the ends 72 of the blade 66 is joined to one of the ends 84 of the sheath 76 by a flexible hinge strap 88. The hinge strap 88 is integrally formed with the two components 60, 62 so as to form a clip 58 of unitary construction. Though the clip 58 is formed of a relatively rigid plastic material, such as polyethylene or polypropylene, the strap 88 is nonetheless highly flexible. Note that the width of the strap 88 is wider than the blade 66 and substantially the same as the width of the sheath 76 to reduce the risk of the blade 66 twisting out of alignment with the sheath 76, and to increase the reliability of the hinge strap 88.

The sheath 76 is provided with slit-like openings 90, 92. The first opening 90 is located at the hinged end 84 of the sheath 76 and is formed by a steel blank (not shown) used in the molding process. The second opening 92 is located at the end 86 of the sheath 76 opposite the hinged end 84 and cooperates with a latch element 94. The latch element 94 is integral with the blade 66 and includes a tapered edge 96 and a shoulder 98. As shown in FIG. 8, upon closing the clip 58, the tapered edge 96 slidably engages the end 86 of the sheath 76 opposite the hinged end 84. When the shoulder 98 clears the lip 100 of the end 86, the latch element 94 springs back towards its initial position, engaging the shoulder 98 of the latch element 94 with the lip 100 of the end 86, holding the two components 60, 62 in a latched condition. An end 102 of the latch element 94 protruding through the second opening 92 in the sheath 76 serves as a lever for urging the latch element 94 into an unlatched position.

As shown more particularly in FIG. 9, the hinged end 72 of the blade 66 includes a safety lock 104 comprising a smoothly-curved cutout 106 of a generally semi-circular outline that matingly engages a convex shoulder 108 within the channel 82 proximate the hinged end 84 of the sheath 76. The safety lock 104 is positioned below the lip 100 of the end 86 opposite the hinged end 84. The convex shoulder 108 also serves as a bearing surface for the camming of the blade 66 upwardly when it engages the cut-out 106 of the blade 66. The width of the blade 66 is equivalent to or slightly less than the width of the channel 82.

When the neck 16 of the ice pack 10 is folded about the edge 68 of the blade 66, and the clip 58 is closed in a manner as is shown in FIG. 3, the neck 16 becomes tightly closed in the clip 58, thereby sealing the ice pack 10 against leakage through the mouth 14. This allows the ice pack 10 to be filled, sealed, and used and after an initial use, to be opened and drained, refilled and re-sealed, and then reused. Hence, a refillable, reusable ice pack 10 is provided. In the event that the hinge strap 88 becomes damaged and/or broken, the safety lock 104 ensures that the clip 58 remains in a closed condition until such time that the latch element 94 is intentionally released.

Referring now to FIGS. 1 through 6, a plurality of ties 54, 56 in the form of strips or straps extend laterally of a longitudinal axis L of the ice pack 10. As shown more particularly in FIG. 3, the ties 54, 56 facilitate maintaining the ice pack 10 against the localized region of the patient P receiving treatment. The ties 54, 56 are preferably of a translucent or transparent white, spunlaced polyester or a combination of polyester and rayon, similar to the material of the outer layers, 32, 34 of the ice pack 10. The ties 54, 56 are located proximate the top and bottom of the reservoir 12 of the ice pack 10. The ties 54, 56 are long enough so as to permit the ice pack 10 to be attached to any localized region of the patient P requiring treatment. A matingly engageable fastener such as a hook and loop type fastener (not shown) may be attached to the straps so as to permit the ice pack 10 to be quickly and easily applied and removed.

Figure 12:
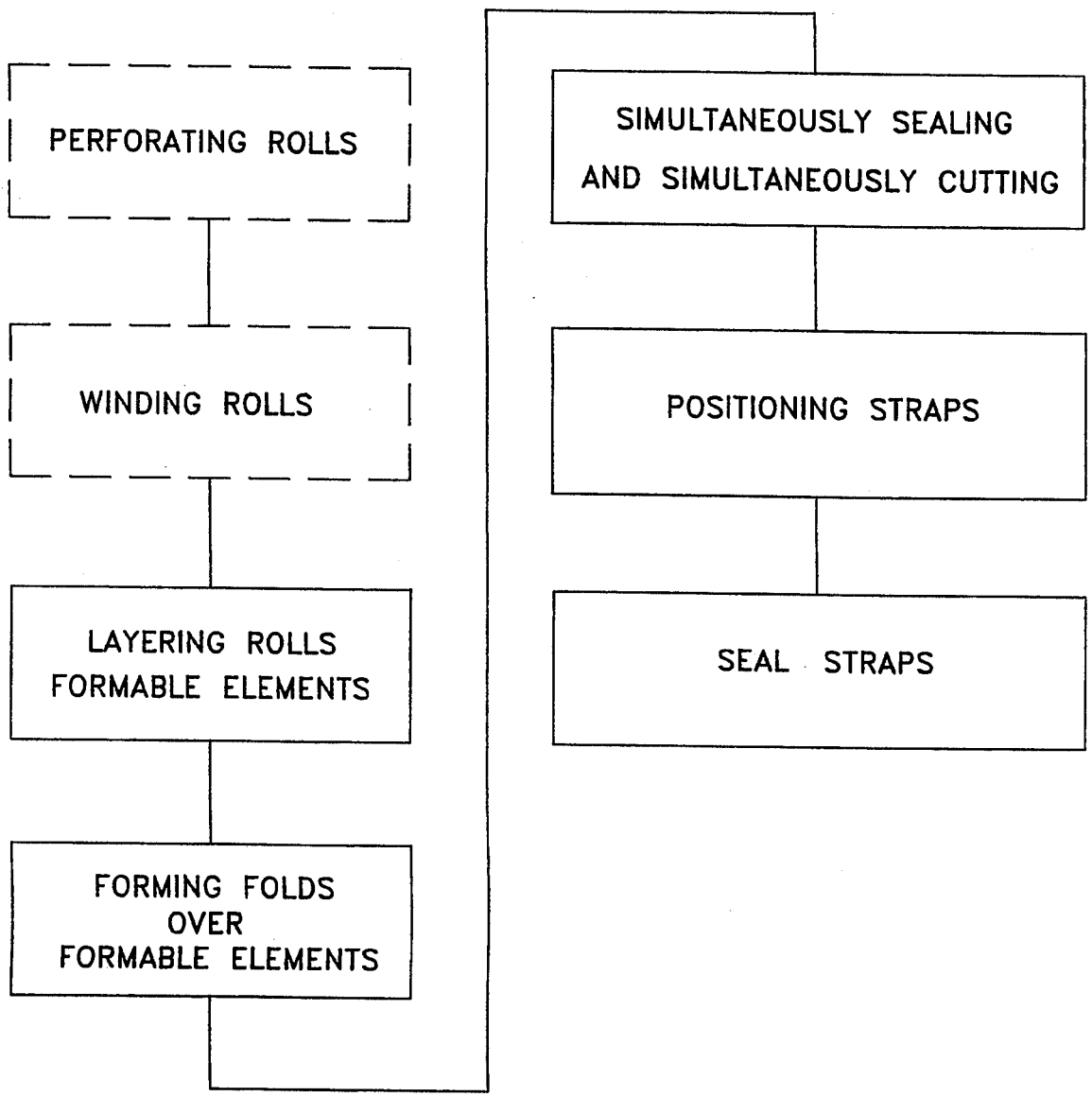
FIG. 12 is a flow diagram representing a process by which the ice pack is produced.

Referring now to FIG. 12, a method for fabricating the ice pack 10 is shown. Initially, foam material is perforated with a rotary perforating machine and is wound on rollers. Two separate rolls of foam material are required, each roll being uniquely perforated.

Subsequently, a plurality of rolls of material are layered together. At least eight rolls would be used to produce the ice pack 10 shown in FIGS. 4 and 5, and nine would be required to produce the ice pack shown in FIG. 6. The rolls are layered together on the heat sealing and cutting machine with the two inner polyethylene watertight layers 28, 30 juxtaposed one another, an intermediate perforated poly foam layer 36, 38 adjacent each inner layer 28, 30, an outer non-woven material layer 32, 34 contiguous to each intermediate layer 36, 38, and a formable element material 46, 48 adjacent the outer material layer 32, 34. Preferably, the intermediate layers 36, 38 do not extend beyond the juncture of the reservoir 12 and the neck 16.

Prior to sealing and cutting of the ice pack 10, the edges of each inner and outer layer 28, 30 and 32, 34 bordering the mouth 14 are folded in opposing directions over respective forming elements 46, 48 and are then sealed, such as with a rotary sealer, a heat sealer, or a sonic sealer, in this folded attitude sealing the formable elements 46, 48 inside the fold 50, 52.

At this point, we have a mouth 14 and neck 16 formed of two plies 22, 24, each having at least two layers 28, 32 and 30, 34, with the formable elements 46, 48 enclosed in the folds 50, 52 proximate the opening 26 of the mouth 14 and a reservoir 12 formed of two plies 22, 24 of at least three layers 28, 36, 32 and 30, 38, 34. Except for along the opening 26 of the mouth 14, these two plies 22, 24 are then heat sealed together about the periphery thereof in the shape of a dumbbell and are simultaneously cut along the seal.

In addition to being sealed about the edges, the mouth 14 is provided with a seal extending diagonally from each side of the neck 16 to respective sides of the mouth 14 so that the mouth 14 tapers from the opening 26 thereof to the opening 18 of the neck 16, thus forming the funnel 20. The formable elements 46, 48 are enfolded within the folds 50, 52 along the mouth 14 to assist in opening the same and forming the funnel 20 and maintaining the shape of the funnel 20 while filling the reservoir 12 with ice I.

The ties 54, 56 are positioned proximate the top and bottom of the reservoir 12 and are heat sealed, sonically welded, or sewn along the side edges thereof.

It should be noted that the sealing of the folds 50, 52, about the periphery of the ice pack 10, of the mouth 14, and of the ties 54, 56 may be accomplished in one or more steps. It should also be noted that the cutting along the seal could be such that a tear line created by a series of nicks in the non-heated cutting die is provided to permit the ice packs to remain connected in series throughout the manufacturing process until such a point that the individual ice packs may be readily separable as desired by tearing along the tear line.

It is also to be understood that the present invention is not limited to the embodiments described above, but encompasses any and all embodiments within the scope of the following claims.

We claim:

1. An ice pack, comprising:
   a) a reservoir for receiving contents therein, said reservoir having:
      1) a first side; and
      2) a second side joined to said first side, said second side incorporating means for providing a greater heat exchange rate than said first side, whereby a temperature differential is provided between said second side and said first side;
   b) a mouth for receiving contents therethrough to fill said reservoir, said mouth being integral with said reservoir;
   c) means for retaining contents in said reservoir, said retaining means being attachable at a juncture between said reservoir and said mouth; and
   d) said first and second sides each including an inner layer, an outer layer, and an intermediate layer interposed between said inner and outer layers, said inner layers being of sheet material impervious to liquids and each said intermediate layer being of a non-absorbent material and including perforations formed therethrough, said perforations in said intermediate material of said first side being distinct from said perforations of said intermediate layer of said second side, whereby a distinction in said perforations between said first and second sides forms the temperature differential between said first and second sides.

2. The ice pack according to claim 1, further including a narrow neck providing a passage for the contents therethrough from said mouth to said reservoir, said neck being integral with said reservoir and said mouth and further being intermediate said reservoir and said mouth, said juncture between said reservoir and said mouth being formed by said neck.

3. The ice pack according to claim 2, wherein said neck has a restricted, squared off opening and said mouth has an opening which tapers inwardly toward said opening of said neck so as to produce a frustoconical-shaped funnel.

4. The ice pack according to claim 1, wherein said first and second sides are fabricated of multi-layered, pliable material plies sealed together so as to provide an opening in said mouth.

5. The ice pack according to claim 1, further including an identifiable visual characteristic which distinguishes said first side from said second side, whereby said identifiable visual characteristic enables the temperature differential between said first and second sides to be visually discerned.

6. The ice pack according to claim 1, wherein said first side carries a first color and said second side carries a second color which is visually distinguishable apart from said first color, said identifiable visual characteristic being formed by said first and second colors.

7. The ice pack according to claim 1, wherein said mouth includes:
   1) an opening located at an upper end thereof; and
   2) means for selectively forming said mouth into a funnel, whereby said forming means may be selectively manipulated to form said funnel and enable said funnel to retract.

8. The ice pack according to claim 7, further including a fold adjacent said opening of said mouth and wherein said forming means includes a formable element enclosed within said fold, whereby
said formable element is selectively manipulated to open said opening of said mouth to create said funnel and to close said opening of said mouth to retract said funnel into a substantially flattened posture.

9. The ice pack according to claim 8, further including means for harnessing said mouth in a folded attitude against said reservoir, whereby
said mouth, when said funnel is retracted in said substantially flattened posture, is foldable so as to be harnessed in said folded attitude against said reservoir by said harnessing means and thereby becomes substantially unobtrusive.

10. The ice pack according to claim 1, wherein said retaining means includes a clip attachable about said juncture between said reservoir and said mouth, whereby
said juncture between said reservoir and said mouth is tightly-closed within said clip, thereby sealing said ice pack against leakage from said reservoir, thus allowing said ice pack to be filled, sealed, and used and after an initial use, to be opened and emptied, refilled and resealed, and then reused.

11. The ice pack according to claim 10, wherein said clip includes:
a) a first component;
b) a second component;
c) means for hingedly joining said first component to said second component; and
d) means for cooperatively latching said first component together with said second component in a closed condition, whereby
said first and second components are pivotally movable relative to one another so as to selectively matingly engage and disengage one another.

12. The ice pack according to claim 11, wherein said joining means includes:
a) a hinge strap integrally formed with said first component and said second component, said hinge strap having a width dimensioned and configured so as to reduce a risk of said first and second components twisting out of alignment with one another.

13. The ice pack according to claim 12, wherein said joining means further includes:
a) means for retaining said clip in said closed condition until such time that said latching means is intentionally released, whereby
if said strap becomes damaged and broken, said retaining means of said joining means provides supplemental support to ensure said clip is retained in the closed condition.

14. The ice pack according to claim 1, further includes a plurality of tie straps for maintaining said ice pack against a localized region of a patient receiving treatment, said tie straps each extending laterally of a longitudinal axis of said ice pack and being located proximate a top end and a bottom end of said reservoir.

15. An ice pack, comprising:
a) a reservoir for receiving contents therein, said reservoir having:
1) a first side; and
2) a second side joined to said first side;
b) a mouth for receiving contents therethrough to fill said reservoir, said mouth being integral with said reservoir, said mouth including:
1) an opening located at an upper end thereof; and
2) means for selectively forming said mouth into a funnel, whereby
said forming means may be selectively manipulated to form said funnel and enable said funnel to retract;
c) means for retaining contents in said reservoir, said retaining means being attachable at a juncture between said reservoir and said mouth; and
d) said first and second sides each including an inner layer, and outer layer, and an intermediate layer interposed between said inner and outer layers, said inner and outer layers being of sheet materials impervious to liquids, and each said intermediate layer being of a non-absorbent material and including perforations formed therethrough, said perforations in said intermediate material of said first side being distinct from said perforations of said intermediate layer of said second side, whereby
a distinction in said perforations between said first and second sides forms a temperature differential between said first and second sides, 16. The ice pack according to claim 15, further including a narrow neck providing a passage for the contents therethrough from said mouth to said reservoir, said neck being integral with said reservoir and said mouth and further being intermediate said reservoir and said mouth, said juncture between said reservoir and said mouth being formed by said neck.

17. The ice pack according to claim 16, wherein said neck has a restricted, squared off opening and said mouth is tapered inwardly from said opening of said mouth to said opening of said neck so as to taper said funnel into a frustoconical shape.

18. The ice pack according to claim 15, wherein said first and second sides are fabricated of multi-layered, pliable material plies sealed together so as to provide said opening of said mouth.

19. The ice pack according to claim 15, wherein said second side incorporates means for providing a greater heat exchange rate than said first side, whereby
the temperature differential is provided between said second side and said first side.

20. The ice pack according to claim 19, further including an identifiable visual characteristic which distinguishes said first side from said second side, whereby
said identifiable visual characteristic enables the temperature differential between said first and second sides to be visually discerned.

21. The ice pack according to claim 19, wherein said first side carries a first color and said second side carries a second color which is visually distinguishable apart from said first color, said identifiable visual characteristic being formed by said first and second colors.

22. The ice pack according to claim 15, further including a fold adjacent said opening of said mouth and wherein said forming means includes a formable element enclosed within said fold, whereby
said formable element is selectively manipulated to open said opening of said mouth to create said funnel and to close said opening of said mouth to retract said funnel into a substantially flattened posture.

23. The ice pack according to claim 22, further including means for harnessing said mouth in a folded attitude against said reservoir, whereby said mouth, when said funnel is retracted in said substantially flattened posture, is foldable so as to be harnessed in said folded attitude against said reservoir by said harnessing means and thereby becomes substantially unobtrusive.

24. The ice pack according to claim 15, wherein said retaining means includes a clip attachable about said juncture between said reservoir and said mouth, whereby said juncture between said reservoir and said mouth is tightly closed within said clip, thereby sealing said ice pack against leakage from said reservoir, thus allowing said ice pack to be filled, sealed, and used and after an initial use, to be opened and emptied, refilled and resealed, and then reused.

25. The ice pack according to claim 24, wherein said clip includes:
   a) a first component;
   b) a second component;
   c) means for hingedly joining said first component to said second component; and
   d) means for cooperatively latching said first component together with said second component in a closed condition, whereby said first and second components are pivotally movable relative to one another so as to selectively matingly engage and disengage one another.

26. The ice pack according to claim 25, wherein said joining means includes:
   a) a hinge strap integrally formed with said first component and said second component, said hinge strap having a width dimensioned and configured so as to reduce a risk of said first and second components twisting out of alignment with one another.

27. The ice pack according to claim 26, wherein said joining means further includes:
   a) means for retaining said clip in said closed condition until such time that said latching means is intentionally released, whereby
   if said strap becomes damaged and broken, said retaining means of said joining means provides supplemental support to ensure said clip is retained in the closed condition.

28. The ice pack according to claim 15, further includes a plurality of tie straps for maintaining said ice pack against a localized region of a patient receiving treatment, said tie straps each extending laterally of a longitudinal axis of said ice pack and being located proximate a top end and a bottom end of said reservoir.

* * * * *